United States Patent [19]
Mardirosian

[11] 4,188,674
[45] Feb. 19, 1980

[54] CONTACT LENS SAVING DEVICES

[76] Inventor: Louis C. Mardirosian, 308 S. Walnut St., Apt. A, Carmi, Ill. 62821

[21] Appl. No.: 915,930

[22] Filed: Jun. 15, 1978

[51] Int. Cl.² .............................................. E03C 1/26
[52] U.S. Cl. ...................................................... 4/292
[58] Field of Search ................... 4/286, 292, 189, 190, 4/290, 295, 289, 291

[56] References Cited
U.S. PATENT DOCUMENTS

| | | | |
|---|---|---|---|
| 1,996,279 | 4/1935 | Dillon | 4/292 |
| 2,518,205 | 8/1950 | Vinokor | 4/292 |
| 3,083,819 | 4/1963 | Entzminger | 4/292 |
| 3,316,562 | 5/1967 | Van Dyke et al. | 4/286 |
| 4,067,072 | 1/1978 | Izzi | 4/292 |

*Primary Examiner*—Lenard A. Footland
*Attorney, Agent, or Firm*—Blair, Brown & Kreten

[57] ABSTRACT

This invention relates in general to a contact lens saving device fabricated of plastic or a suitable material. Said device being composed of a locating ring which fits over the metal closure stopper of a sink or basin, and having an upper structure being so perforated with holes which allows for free passage of water in a sink or basin while preventing the loss of a contact lens which on occasion is dropped into the sink or basin by accident. The device has a gripper knob for the insertion or removal into some drain openings where it is necessary and is completely portable.

4 Claims, 6 Drawing Figures

CONTACT LENS SAVING DEVICES

PRIOR ART STATEMENT

Now refering to the improvements in my contact lens saving device over any prior art wherein, the advancement of contact lenses; the conventional (polymethymethacrylate) hard lenses, the more recent (polymocon) soft lenses, and the recently introduced (cabufocon) semi-soft lenses are different in their physical makeup and the care needed to disinfect and clean their surfaces are of an entirely different nature therefore, it is imperative that all contact lens wearers should be given the opportunity to provide themselves with a total contact lens saving device which in its physical embodiment is totally independent of any combined contact lens carrier and drain guard unit.

The preparation, rinsing, cleaning and insertion of hard contact lenses is done directly over the sink basin whereas, the newer soft contact lenses are cleaned in an entirely different manner wherein, the soft contact lens disinfecting units require positioning on Formica topped surface areas such as those found in modern bathrooms wherein, these units are electrical in nature and their outer surfaces become very hot while in their disinfecting operation. Therefore, it is imperative to offer to the public a total contact lens saving device wherein, its total physical embodiment will accommodate the two most commonly used bathroom and restroom sink drains, eliminate the loss of contact lenses into such drains, while allowing for the free passage of water into such drains.

Another improvement in my invention is that it allows complete portability and is totally independent from any combined lens carrier and guard unit that may be presently on the market wherein, such devices have their shortcomings in that they must be removed from the sink following their usage and in the event contact lens adjustments are necessary such devices must be inserted into the sink thus wasting time whereas, my invention being totally free from any contact lens carrier units may remain permanently in the sink thus allowing for the normal daily routine that such sinks provide.

Another improvement of my invention device over the prior art is that placement of the prior art into the sink will result in the contraction of chemicals, abrasives or small bits of hair upon the surface area of such a device whereby, these foreign bodies may eventually find their way into the carrier chambers where the contact lenses are stored in such combination lens carriers and guard units an example of which is disclosed in U.S. Pat. No. 3,083,819 of Entzminger wherein, my invention is totally void of such carrier chambers. Upon my critical testing of many types of lens saving devices which I constructed, I have come to the conclusion that a circular ring base collar at the base of such a device is an absolute necessity and without such a collar the grasping and retrievel of a dropped contact lens is awkward, cumbersome and next to impossible to perform therefore, cite this as still another improvement in my contact lens saving device.

Continuing, another improvement of my invention device is its total flexibility in its functional applications in that my device allows for the free passage of water into the sink orfice while at same time preventing damage or loss of a contact lens wherein, this complete flexibility is provided by the removal of the upper structure of the device to accommodate those sinks that do not have built-in metal stopper disks and in lieu of the usual rubber stopper device commonly used which does not allow for the free passage of water whereby, in the event the contact lens is dropped into the sink of standing water a "fishing out" process will be necessary for lens retrievel thus wasting time and causing possible surface damage to the delicate lens.

Another improvement of my invention is its secondary adaptor structure which may be used in lieu of a rubber stopper for total water stoppage in a sink or allow for the free passage of water into the sink orifice.

It is to be understood that no "crumb cup" strainers such as those sometimes found in common bathroom sinks were disclosed to me by my searchers wherein, the above reference is made to the metal type cup devices that are used in lieu of the metal stopper closure disk whereby the use of such "crumb cups" will allow for the passage of a contact lens by way of their designs wherein, their metal edges are unpolished and allow for the scratching of a contact lens coming into physical union with such a device.

Continuing, the "crumb cups" are of such a design that retrievel of a contact lens from their edifice is impossible (due to the depth of the cup) while in their positioning in a sink orfice thereby, removal of the "crumb cup" is necessary to recover the contact lens thereby, leaving the orifice in an uncovered state thus creating a situation wherein, accidental droppage of the contact lens into the sink at this moment would result in the loss of the contact lens into the open and uncovered orfice.

| Patent No. | Inventor | Issued | Title |
|---|---|---|---|
| 2,518,205 | Vinokor | 8-8-50 | Sieve or grid for sinks |
| 2,695,411 | Vinokor | 11-30-54 | Grid for outlet or sinks |
| 3,083,819 | Entzminger | 4-2-63 | Combined contact lens carrier and drain gaurd |
| 3,161,360 | Levine | 12-15-64 | Gaurd for garbage disposal |
| 3,788,485 | Bruning | 1-29-74 | Drain gaurd for contact lens |
| 3,972,078 | Maki | 8-3-76 | Drain sieve |
| 4,049,551 | Otzen | 9-20-77 | Safety device for receptacle |

The Entzminger U.S. Pat. No. 3,083,819 is the most closely related patent to which my application relates. The improvements of my invention to which I have related to are described in the summary, the embodiment descriptions, and the drawings, and the claims setforth herein.

SUMMARY OF THE INVENTION

Therefor, a primary object of this dual purpose lens saving device is that upon placing the device over the metal disk-type stopper in a sink orifice, the prevention of damage or the prevention of loss of a contact lens into the orfice will result. Upon removal of the upper structure of such a device, this upper structure will fit into the standard orfice in most bathrooms or restroom sinks thus preventing the damage or loss of a contact lens into this type orfice while at the same time allowing for the free passage of water into the orfice of a sink or basin.

Another object is to provide a dual purpose contact lens saving device wherein, the upper structure of said device may be attached to the lower structure by means of threading, snaps or otherwise connected to the lower structure lens saving device and wherein, the lower structure having a shape and size suitable to cover most metal disk-like stopper structures in sinks of this type and being so constructed with a plurality of holes small enough to prevent the loss of a contact lens while at the same time allowing for the free passage of water into the orfice of a sink or basin.

Another object is to provide a dual purpose lens saving device wherein, the lower structure of said device may be attached to the upper structure by means of threading, snaps or otherwise connected to and made a part of the upper structure wherein, the upper structure of the lens saving device is of a shape and size suitable to be inserted into the orifice of a bathroom sink or basin and being so constructed with a plurality of holes small enough to prevent the loss of a contact lens while at the same time allowing for the free passage of water into the orfice of such a sink or basin.

Continuing, another object of the dual purpose lens saving device is to be so constructed of such a material that will not inflict damage or scratching to the delicate surface of a contact lens whereby, this objective is embraced by the molding or shaping or forming of such a device from plastic or other like material.

Yet another object of the device is to allow for the ease of retrievel of the disk-like upper portion of the structure wherein, said function is embraced by the attachment of an integral pullout knob which allows for the ease of insertion or withdrawal from a sink or basin orfice of that type necessitated by such a need.

A further object is to provide a modified version of a dual purpose lens saving device wherein, the construction of an upper portion of the structure affords an optional hinge-like top cover in lieu of the pullout knob portion wherein, said top cover while in its closed position has the capacity to stop the flow of water through the small holes in the disk-like portion of the aforementioned upper structure thus eliminating the need for a second stopper. (I.e. rubber type). Continuing, upon the opening of this top cover, the free passage of water through the plurality of holes will result and the small diameter of such holes will restrict the loss of a contact lens into a basin sink orfice. Likewise, this type upper structure may be attached by means of threading, snaps or otherwise connected to the lower structure and be made a part thereof.

The construction of the aforegoing improvements in the present state of the art will hereinafter be disclosed and more fully described. Other objects, advantages and special features of this invention device will become apparent upon the consideration of the following descriptions of the accompanying drawings, in which:

DESCRIPTION OF THE EMBODIMENT

Figure 1:
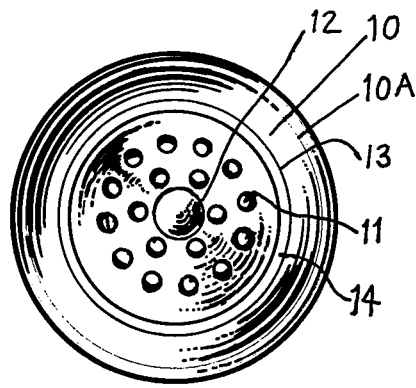
FIG. 1 is a perspective view of the invention device constructed to be in accordance with the invention.
Figure 2:
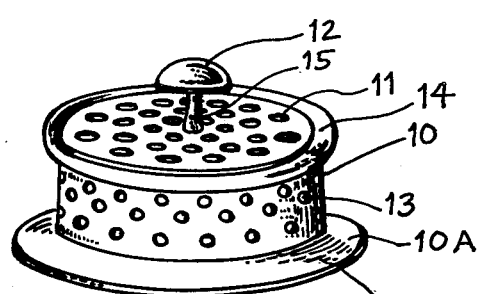
FIG. 2 is a side perspective view of the invention rendered in such a manner to illustrate the uniqueness of its novelty.
Figure 3:
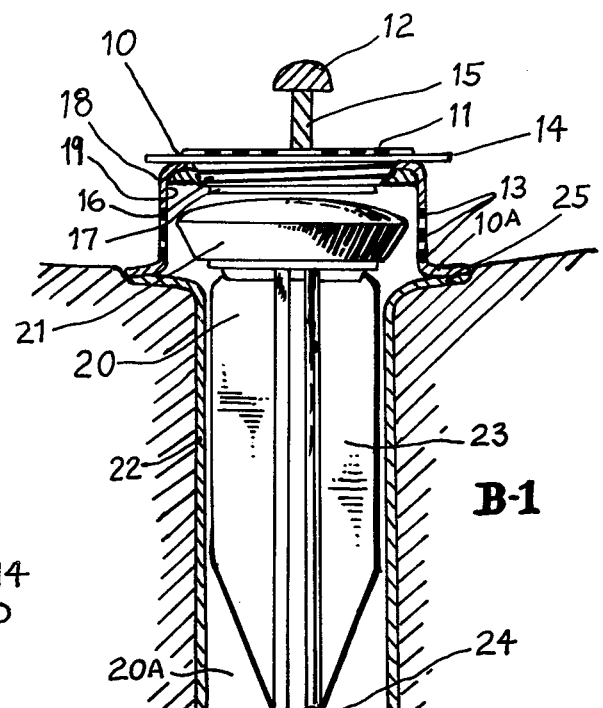
FIG. 3 is a side sectional view of the invention fitted over an OPEN disk-like metal stopper.

Referring now to the drawings which are enclosed herein and made a part of this patent application, particularly to FIG. 1-2-3, a dual purpose contact lens saving device of which its total embodiment is exemplified at numeral 10. The device 10 being comprised of an angular or horizontal or bent horizontal ring at its circular base 10A of which in its upper structure are formed a plurality of holes or openings 11 & 13 through which water may flow freely when placed at 25 the opening orfice of a sink or basin while at the same time preventing the loss of a contact lens.

Figure 4:
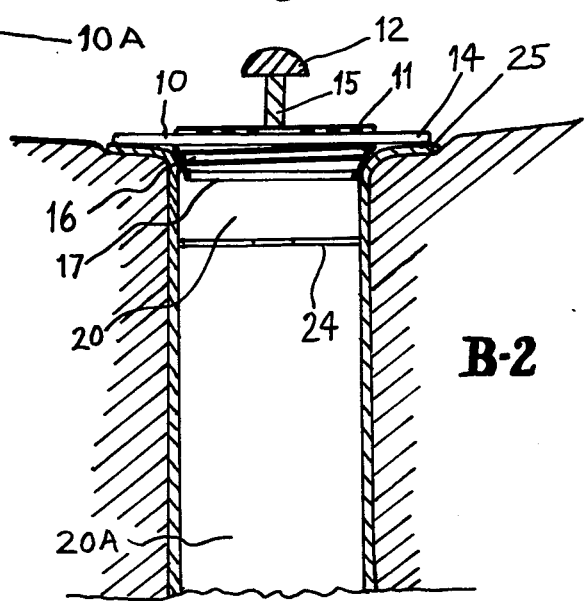
FIG. 4 is a side sectional view of the invention fitted into a sink orfice. (Upper structure only fits into this type sink).

Attached to and made an integral part of the upper structure 10 is a vertical stem 15 upon which is embraced at its top portion, a hemispherical ball 12 by which insertion or withdrawal may be made at the sink or basin B-2 into orfice 20 in FIG. 4.

FIG. 2 As seen in FIG. 2, the lower structure 10 of the device is so perforated with a plurality of holes 13 which allows for the free passage of water into the sink or basin orifice 20 while preventing the loss of a contact lens. By virtue of the outer rim 14 being of a greater diameter than that of the orifice 20, FIG. 4, the upper structure 10 when removed from the lower structure 10 may be placed into the orifice 20 and thus allow for the free passage of water while at the same time preventing the loss of a contact lens.

Withdrawal of the upper section 10 from the orifice 20, FIG. 4, is made with ease by pulling on the knob 12 attached to the top stem 15.

The lower portion of the structure 10 is removed from the upper portion of structure 10 by way of threads 16, disposed on a cylindrical sleeve FIGS. 3 & 4, while lateral shifting in the orifice 20 is controlled by the extension flange 17 of the upper structure 10 thus allowing for the free passage of water into a sink or basin while at the same time preventing the loss of a contact lens.

FIG. 3 As seen in FIG. 3, the inner diameter 18 of the lower portion of structure 10 is so constructed to fit over the outside diameter of the metal closure stopper 21 in such a manner as to allow for the free passage of water into the orifice 20 through the holes provided 13 thus preventing the loss of a contact lens into the orifice 20.

FIGS. 3 & 4 Relating to the basin structures wherein, the inner wall portion of the drain orifice 20 encompasses the stopper guide posts 23 which align the stopper closure 21 into the orifice 20 when the element 24 is used to raise and lower the stopper closure 21 in the drain bore 20A. The visible portion of the drain bore 25 is shown and the usual trapping device 24 is part of most drain bores 20A of this variety of the basin B-2.

Figure 5:
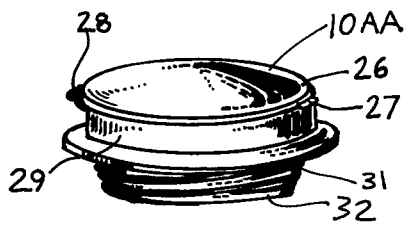
FIG. 5 is a side perspective view of the optional cover-type device with the cover in a closed position.
Figure 6:
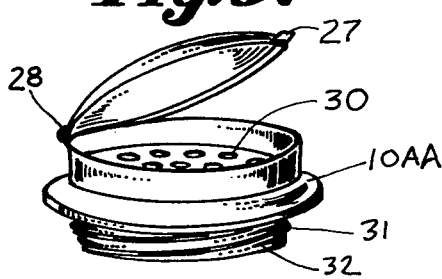
FIG. 6 is a side perspective view of the optional cover-type device with the cover in an open position.

Relating to the secondary type of upper structure 10AA of which an exemplary embodiment is illustrated in FIGS. 5 & 6, which show an upper lid or closure cover 26 with an attached opening tab 27 the inner diameter so constructed and hinged 28 to maintain proper alignment with the outer diameter of its lower portion 29 and being so perforated with a plurality of holes 30 as to allow for the free passage of water while the aforementioned lid or cover 26 is in an open position. Upon the closing of the cover 26 a water tight seal is secured between the cover 26 and the lower portion 29 thus eliminating the need for a separate rubber stopper device such as is commonly used in most sinks of this variety.

Continuing, the said device 10AA being so constructed with integral threading 31 to conform with and be attached or otherwise secured to the upper portion of the lower structure 10 shown in FIG. 1-2-3, while lateral shifting in the orifice 20, FIG. 4, is controlled by the extension flange 32 of the structure 10AA. Thusly the said structure 10AA as shown will provide for the free passage of water through its plurality of holes 30 while preventing the loss of a contact lens and will stop the flow of water into the orifice 20 of a sink or basin thereby entitling this structure 10AA to form a total configuration in itself or to be used in conjunction with the upper portion of the lower structure 10 as seen in FIG. 1-2-3.

While various embodiments of this invention are revealed and described, the total description of my dual purpose lens saving device inventions are of a detailed nature so that a specific embodiment of them may be set forth as required, but it is to be understood that various modifications of their detail, rearrangement and multiplication of their parts may be retorted to without departing from their spirit, essence, novelty or scope.

Therefore, I desire to protect my invention by Letters Patent and what I claim is:

1. A contact lens saving device comprising in combination:

a plate having a plurality of openings therein, an outer rim surrounding and underlying said plate fastened thereto, a first cylindrical sleeve underlying said outer rim fastened thereto, and provided with threads on an outer face thereof which terminates in an extension flange which retards lateral translation of said device when disposed in a drain opening of a sink basin, whereby said openings are large enough to permit the egress of water from the basin but small enough to trap a contact lense thereagainst and in which a second sleeve having inner threads thereon engage the threads of said first sleeve, said second sleeve having a greater verticle dimension than said first sleeve, an annular base surrounding said second sleeve at its lowermost extent, and holes on said second sleeve whereby said second sleeve serves to raise said device to allow room for a conventional basin stopper to open and close.

2. The device of claim 1 in which said device has centrally disposed thereon an upstanding stem which terminates in a substantially hemispherical ball to facilitate removal of said device.

3. The device of claim 1 in which said top plate has an annular rim upstanding therefrom having a hinge along one top edge thereof connected to a cover which can pivot from an opened to closed position.

4. The device of claim 3 in which a tab is disposed on said cover opposed from said hinge to facilitate orientation.

* * * * *